US007145289B2

(12) United States Patent
Yamazaki et al.

(10) Patent No.: US 7,145,289 B2
(45) Date of Patent: Dec. 5, 2006

(54) DISPLAY DEVICE, CAMERA, PERSONAL COMPUTER, AND PORTABLE TELEPHONE

(76) Inventors: Shunpei Yamazaki, c/o Semiconductor Energy Laboratory Co., Ltd., 398, Hase, Atsugi-shi, Kanagawa-ken 243-0036 (JP); Takeshi Fukunaga, c/o Semiconductor Energy Laboratory Co., Ltd., 398, Hase, Atsugi-shi, Kanagawa-ken 243-0036 (JP)

( * ) Notice: Subject to any disclaimer, the term of this patent is extended or adjusted under 35 U.S.C. 154(b) by 14 days.

(21) Appl. No.: 11/083,189

(22) Filed: Mar. 17, 2005

(65) Prior Publication Data

US 2005/0156509 A1   Jul. 21, 2005

Related U.S. Application Data

(63) Continuation of application No. 09/732,049, filed on Dec. 7, 2000, now Pat. No. 6,894,431.

(30) Foreign Application Priority Data

Dec. 15, 1999   (JP)   .................... 11-356736

(51) Int. Cl.
*H05B 33/06* (2006.01)
*H01J 1/62* (2006.01)
(52) U.S. Cl. .................. 313/506; 313/498; 313/505
(58) Field of Classification Search ........ 313/504–512; 257/99–103, 59, 72; 345/87; 315/169.1
See application file for complete search history.

(56) References Cited

U.S. PATENT DOCUMENTS

| | | | |
|---|---|---|---|
| 3,219,865 A | 11/1965 | Vodicka | 313/509 |
| 4,061,837 A | 12/1977 | Hutkin | 428/609 |
| 5,457,356 A | 10/1995 | Parodos | 313/505 |
| 5,532,550 A | 7/1996 | Adler | 313/500 |
| 5,650,640 A | 7/1997 | Stafford et al. | 257/81 |
| 5,703,394 A | 12/1997 | Wei et al. | 257/433 |
| 5,747,363 A | 5/1998 | Wei et al. | 438/5 |
| 5,838,037 A | 11/1998 | Masutani et al. | 257/296 |
| 5,962,959 A | 10/1999 | Iwasaki et al. | 313/310 |
| 5,990,629 A | 11/1999 | Yamada et al. | 315/169.3 |
| 6,091,194 A | 7/2000 | Swirbel et al. | 313/498 |
| 6,121,988 A * | 9/2000 | Uchiyama | 347/208 |
| 6,137,218 A | 10/2000 | Kaneko et al. | 313/495 |

(Continued)

FOREIGN PATENT DOCUMENTS

EP   0 736 913 A2   10/1996

(Continued)

OTHER PUBLICATIONS

European Search Report re application No. EP 00127536.1, dated Dec. 15, 2005.

*Primary Examiner*—K. Guharay
*Assistant Examiner*—Sikha Roy

(57) ABSTRACT

A light-emitting device having the quality of an image high in homogeneity is provided. A printed wiring board (second substrate) (107) is provided facing a substrate (first substrate) (101) that has a luminous element (102) formed thereon. A PWB side wiring (second group of wirings) (110) on the printed wiring board (107) is electrically connected to element side wirings (first group of wirings) (103, 104) by anisotropic conductive films (105a, 105b). At this point, because a low resistant copper foil is used to form the PWB side wiring (110), a voltage drop of the element side wirings (103, 104) and a delay of a signal can be reduced. Accordingly, the homogeneity of the quality of an image is improved, and the operating speed of a driver circuit portion is enhanced.

72 Claims, 8 Drawing Sheets

U.S. PATENT DOCUMENTS

| | | |
|---|---|---|
| 6,168,851 B1 | 1/2001 | Kubota .................. 428/200 |
| 6,175,345 B1 | 1/2001 | Kuribayashi et al. ......... 345/76 |
| 6,225,966 B1 | 5/2001 | Ohtani et al. ................ 345/87 |
| 6,274,978 B1* | 8/2001 | Roach et al. ............... 313/483 |
| 6,353,280 B1 | 3/2002 | Shibata et al. ............. 313/292 |
| 6,370,019 B1 | 4/2002 | Matthies et al. ............ 361/681 |
| 6,384,427 B1* | 5/2002 | Yamazaki et al. ............ 257/59 |
| 6,525,467 B1* | 2/2003 | Eida et al. ................. 313/506 |
| 6,630,687 B1* | 10/2003 | Koyama et al. .............. 257/72 |
| 6,724,149 B1 | 4/2004 | Komiya et al. ......... 315/169.3 |

FOREIGN PATENT DOCUMENTS

| | | |
|---|---|---|
| EP | 0 883 191 A2 | 12/1998 |
| EP | 0 884 782 A1 | 12/1998 |
| WO | WO 99/41787 A1 | 8/1999 |

* cited by examiner

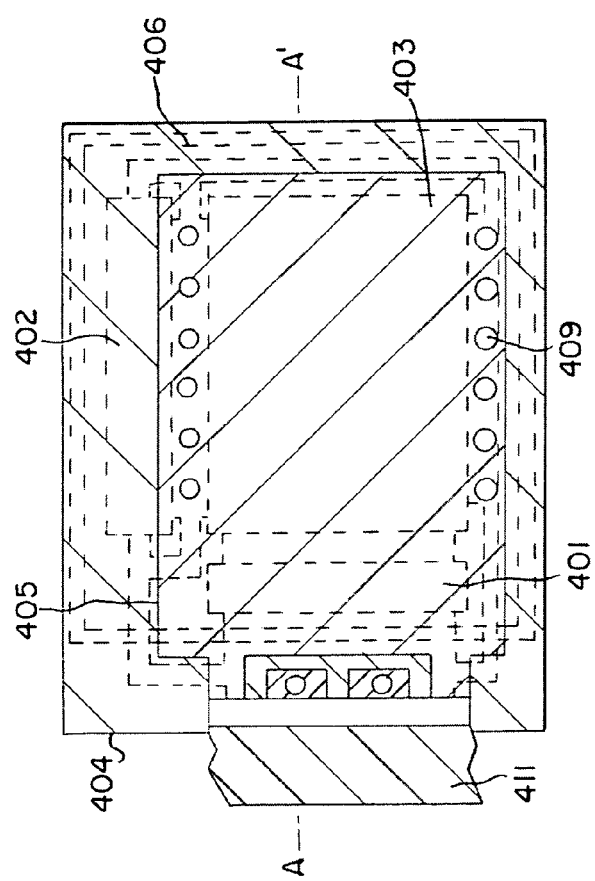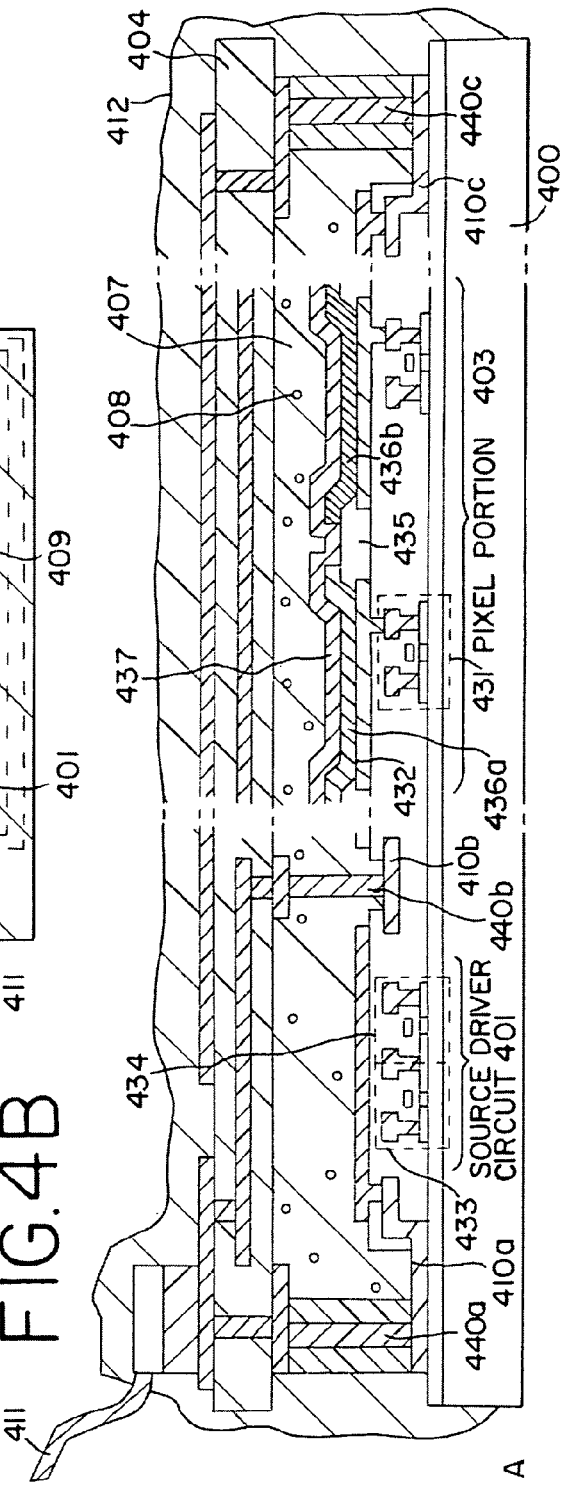
FIG. 4A
FIG. 4B

US 7,145,289 B2

DISPLAY DEVICE, CAMERA, PERSONAL COMPUTER, AND PORTABLE TELEPHONE

This application is a continuation of U.S. patent application Ser. No. 09/732,049 filed Dec. 7, 2000, now U.S. Pat. No. 6,894,431.

BACKGROUND OF THE INVENTION

1. Field of the Invention

The present invention relates to a device having an element (hereinafter referred to as luminous element) that is comprised of a luminous material sandwiched between electrodes (the device will hereinafter be referred to as light-emitting device), and to a method of manufacturing the same. Specifically, the present invention relates to a light-emitting device using a luminous material that provides EL (Electro Luminescence) (hereinafter referred to as EL material).

2. Description of the Related Art

In recent years, development is proceeding in a light-emitting device (EL display device) using a luminous element that utilizes the EL phenomenon of a luminous material (hereinafter referred to as EL element). The EL display device is a display device that uses a luminous element which itself has a light-emitting ability, that is, self-emissive, and hence, unlike a liquid crystal display device, does not need a back light. In addition, the EL display device has merits such as a wide field of vision, light weight, and a low power consumption.

Such an El display device is constructed of a structure that has an EL element composed of an anode, a cathode, and an EL material sandwiched therebetween. By applying a voltage between the anode and the cathode to make a current flow in the EL material, carriers re-couple, whereby the EL element emits light. Such a driving method is called a current drive. However, in the EL display device which has the current drive, there is a problem of a phenomenon in which a voltage drop (also referred to as an IR drop) caused by a wiring resistance occurs. This phenomenon is that the voltage becomes lower as its distance from a power source becomes farther even if it is the voltage of the same wiring. This problem is particularly conspicuous when the wiring becomes long. Thus, it is a large obstacle in making the screen of the EL display device larger.

When the wiring is made of a material such as tantalum, tungsten, or silicon, the EL display device is susceptible to the influence of the wiring resistance, which may become the cause of immensely reducing the homogeneity of the quality of the image. In addition, in case of using a low resistant material such as aluminum or copper, when the draw-around distance is long, then the same thing can be observed, i.e., the aforementioned phenomenon will occur.

The above-mentioned problem will be explained here with reference to FIG. 2. Shown in FIG. 2 is a portion of a pixel portion of an active matrix EL display device. An □n number of pixels denoted by $A_1, A_2, \ldots A_n$ are arranged in the up and down direction (vertical direction) of the diagram. Reference symbol 201 denotes a gate wiring, 202 denotes a source wiring, and 203 denotes a current supply line. Furthermore, a switching TFT 204, a storage capacitor 205, a current control TFT 206, and an EL element 207 are formed in a region that is surrounded by the gate wiring 201, the source wiring 202, and the current supply line 203.

At this point, the voltage of the current supply line 203 drops as the current supply line 203 moves towards the bottom of the diagram due to the influence of the voltage drop. That is, a voltage $V_1$ that was in the upper part of the pixel portion becomes a voltage $V_2$ in the lower part of the pixel portion, becoming a relationship of $V_1 > V_2$. This influence becomes more conspicuous as the area of the pixel portion (image display region) is made larger.

As a result, in case of making the EL elements of each of the pixels emit light in the same brightness, the pixel denoted by $A_1$ and the pixel denoted by $A_2$ will emit light in about the same brightness. However, the brightness of the light emitted by the pixel denoted by $A_n$ declines compared with the pixel denoted by $A_1$ and the pixel denoted by $A_2$. The reason for this originates in that the voltage applied to the EL element of the pixel denoted by $A_n$ has declined due to the voltage drop.

Further, the influence of such voltage drop is imparted not only to the current supply line 203 but also to the gate wiring 201 and the source wiring 202. In other words, there is a concern that the gate wiring 201 may not be able to open a gate of the switching TFT 204 because of the voltage drop. In addition, the source wiring 202 becomes incapable of applying a desired voltage to a gate of the current control TFT 206 due to the voltage drop, leading to a fear that the brightness of the EL element will change or that the EL element will not emit light.

Thus, the transmission of a desired voltage becomes impossible because of the voltage drop which originates in the wiring resistance.

Consequently, a drawback in which there is a considerable loss in the homogeneity of the quality of the image in the pixel portion occurs. Attempts such as contriving to apply a voltage to both ends of the wiring have been made in order to improve the above problem. However, because the wiring is drawn around longer, as a result, the influence of the voltage drop cannot be ignored.

In case of manufacturing a monolithic type light-emitting device in which a driver circuit portion (typically including a gate driver circuit and a source driver circuit) is integrated on the same substrate, the wiring resistance of a wiring that is drawn around between the driver circuit portion and an input terminal of an electric signal becomes a problem. The wiring resistance induces a delay of the electric signal, and therefore there is a concern that the operating speed of the gate driver circuit and the source driver circuit will be reduced.

Thus, drawbacks such as the considerable loss of the homogeneity of the quality of the image and the extreme decline in the operating speed of the driver circuit portion due to the voltage drop which originates in the wiring resistance and the delay of a signal occur.

Such a problem becomes a particularly conspicuous problem in a light-emitting device having a large screen that is several tens inches in diagonal.

SUMMARY OF THE INVENTION

The present invention has been made in view of the above, and therefore has an object to provide a light-emitting device that has a homogenized quality of image by suppressing an influence of a voltage drop which originates in the above-mentioned wiring resistance. Further, another object of the present invention is to suppress a delay of a wiring which electrically connects a driver circuit portion and an input/output terminal to thereby enhance the operating speed of the driver circuit portion.

The light-emitting device of the present invention is constituted of a substrate having a luminous element formed thereon (hereinafter referred to as element-formed substrate or a first substrate) and a hardened large printed wiring board (PWB: Printed Wiring Board), which are electrically connected by a conductor (anisotropic conductive film or a bump), and is characterized in that the resistance of each of the wirings (first group of wirings) formed on the element-formed substrate is reduced.

It is to be noted that the hardened large printed wiring board (hereinafter referred to as printed wiring board or a second substrate) indicates a printed wiring board that has a level of hardness which does not bend or curve to some amount of impact.

Typically, the hardened large printed wiring board refers to a printed wiring board that is formed of a material selected from a glass cloth epoxy, glass cloth heat-resistant epoxy, ceramic, alumina, paper-based phenol, or paper-based epoxy. In addition, it is also possible to use a transmissive glass substrate, a quartz substrate, or a plastic substrate.

BRIEF DESCRIPTION OF THE DRAWINGS

The above and other objects and features of the present invention will be more apparent from the following description taken in conjunction with the accompanying drawings:

FIGS. 4A and 4B are diagrams showing a top structure and a cross-sectional structure of an EL display device, respectively;

DETAILED DESCRIPTION OF THE PREFERRED EMBODIMENTS

Figure 1A:
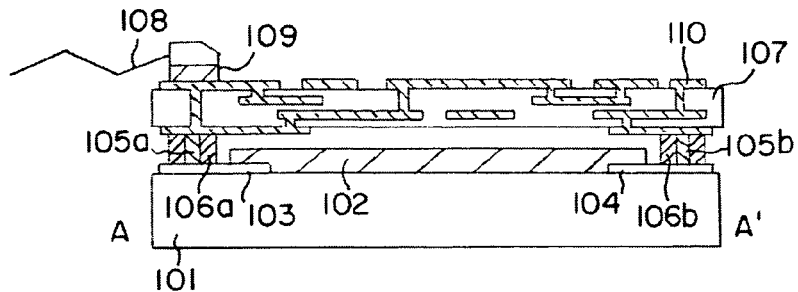
FIGS. 1A and 1B are diagrams showing a cross-sectional structure and a top structure of a light-emitting device, respectively.
Figure 1B:
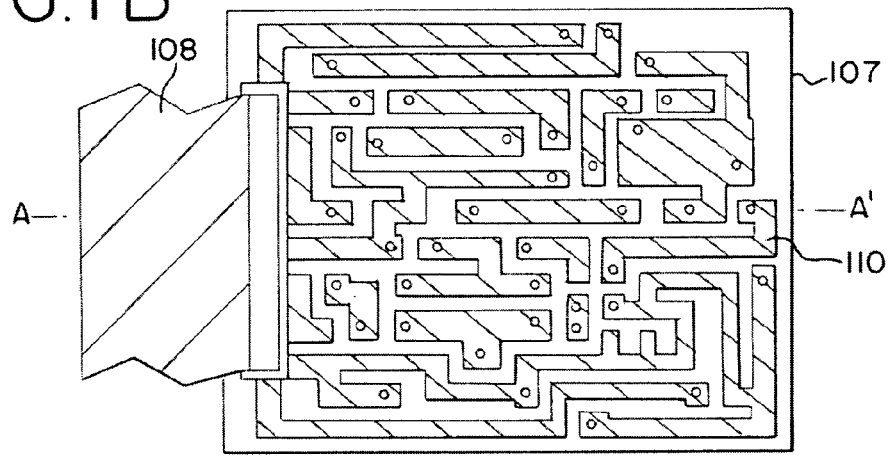
Figure 2:
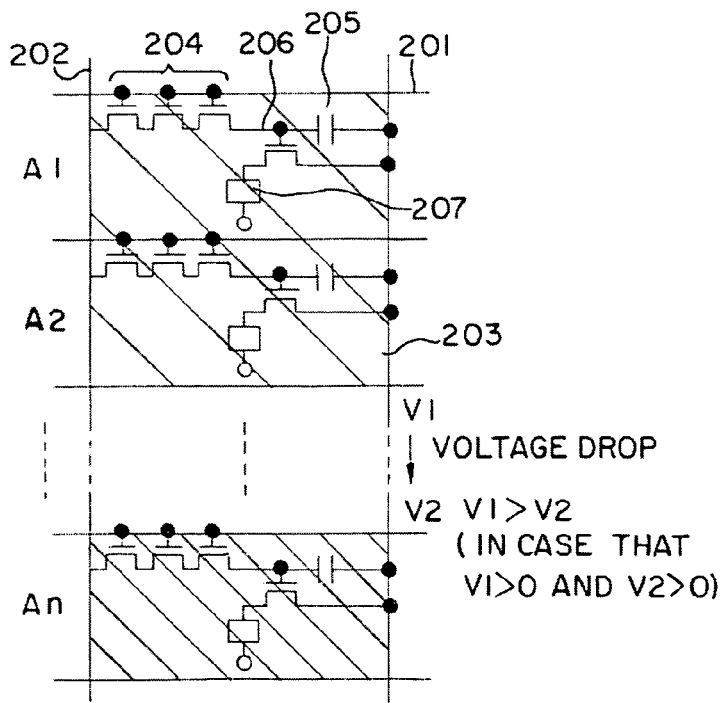
FIG. 2 is a diagram illustrating the change in brightness of a pixel.

The cross-sectional view of the light-emitting device of the present invention is shown in FIG. 1A, and the top view thereof is shown in FIG. 1B. Note that the cross-sectional view taken along the line A–A' of FIG. 1B corresponds to FIG. 1A.

In FIG. 1A, reference symbol 101 denotes a substrate having a luminous element 102 (typically an EL element or a semiconductor diode element) formed thereon. Wirings 103 and 104 for transmitting an electric signal (hereinafter referred to as element side wiring) to the luminous element 102 are formed on the substrate 101. These components correspond to the above-mentioned element-formed substrate. It is to be noted that a glass substrate, a quartz substrate, a plastic substrate, a silicon substrate, a ceramic substrate, or a metallic substrate may be used as the substrate 101.

A printed wiring board 107 is electrically connected to the substrate 101 via conductors 105a and 105b that are provided on the wirings 103 and 104 of the element-formed substrate. It is to be noted that reference symbols 106a and 106b denote sealing agents for bonding the element-formed substrate 101 and the printed wiring board 107 together.

Furthermore, a group of wirings (second group of wirings) are formed on the front surface, the back surface or the interior of the printed wiring board 107. When the wirings are formed in two or more different layers, it is referred to as a multi-layered wiring (or a lamination wiring) in the present specification. On the other hand, when one layer of wiring is formed in either the front surface, the back surface, or the interior, then it is referred to as a single-layered wiring in the present specification.

In the present invention, the printed wiring board 107 may have either the multi-layered wiring or the single-layered wiring.

At this point, an anisotropic conductive film, a conductive paste or a bump can be used as the conductors 105a and 105b. As the bump, typically, a solder bump, a metal bump, a nickel bump, or a copper bump can be used. In addition, resin having metallic particles such as silver and nickel dispersed therein can be used as the conductive paste.

An FPC (Flexible Printed Circuit) 108 is attached to a terminal portion of the printed wiring board 107. Further, a wiring 110 for transmitting an electric signal, which was transmitted to an anisotropic conductive film 109, to the conductors 105a and 105b is formed to a thickness of between 1 and 20 μm (hereinafter referred to as PWB side wiring or the second group of wirings). Typically, a pattern formed of a copper foil, a gold foil, a silver foil, a nickel foil, or an aluminum foil is used as the PWB side wiring 110. Note that though the FPC is a printed wiring board in a broad sense, it is not included in the definition of the printed wiring board in the present invention.

In the light-emitting device of the present invention incorporating the above-mentioned structure, an electric signal transmitted to the FPC 108 is transmitted to the conductors 105a and 105b by the PWB side wiring 110, and then the signal can be transmitted to the luminous element 102 via the element side wirings 103 and 104. At this point, because the PWB side wiring 110 is made of an extremely low resistant wiring, the voltage drop which originates in the wiring resistance can be immensely suppressed, thereby making it possible to transmit nearly equivalent electric signals to the element side wirings 103 and 104. Similarly, the wiring resistance of the PWB side wiring 110 is small, and therefore, the delay of a signal is largely suppressed. Consequently, it is possible to improve the drawback of the reduction in the operating speed of the driver circuit.

Further, a characteristic of the present invention is that a material selected from a glass cloth epoxy, glass cloth heat-resistant epoxy, ceramic, alumina, paper-based phenol, or paper-based epoxy is used as the material of the printed wiring board 107 so that the printed wiring board 107 has an impact-resistant property. As a result, it becomes possible to protect the luminous element from external impact, whereby a highly reliable light-emitting device can be attained.

A case of manufacturing an EL display device by employing the present invention will be explained in Embodiment Mode of the present invention. The top views of the EL display device manufactured by employing the present invention is shown in FIGS. 3A and 3B.

Figure 3A:
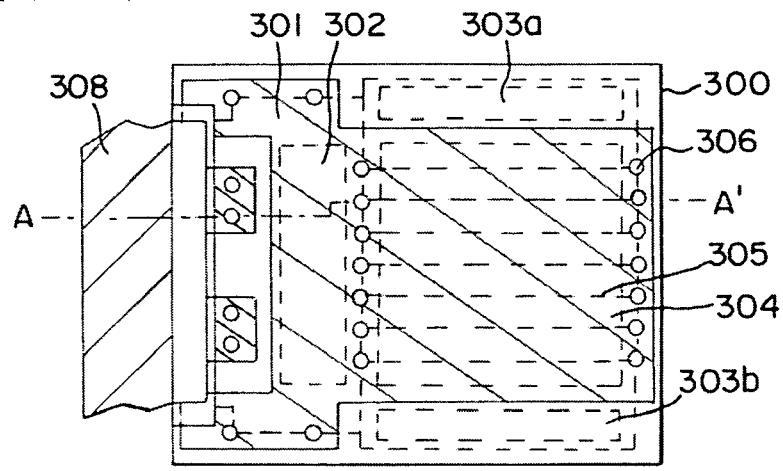
FIGS. 3A and 3B are diagrams showing top structures of a light-emitting device.
Figure 3B:
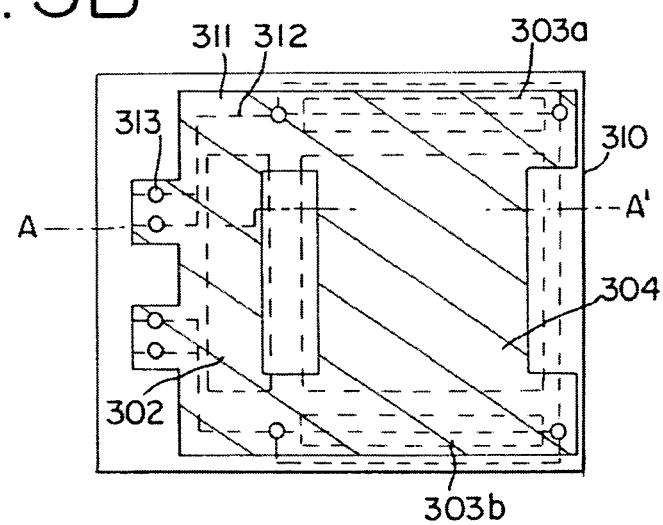
Figure 3C:
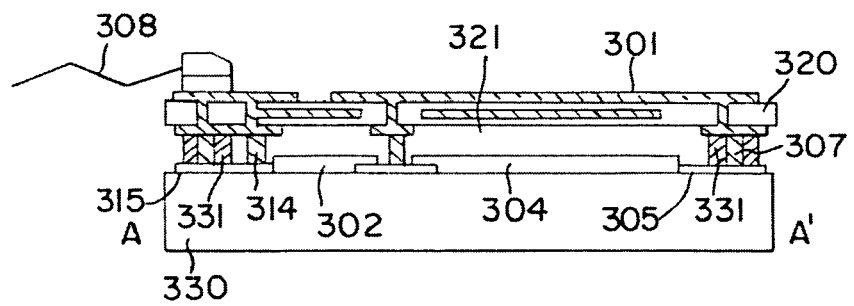
FIG. 3C is a diagram showing a cross-sectional structure thereof.

Note that in Embodiment Mode, the top views of the EL display device are shown in FIGS. 3A and 3B, and the cross-sectional view thereof is shown in FIG. 3C. FIG. 3C is a cross-sectional view taken along the line A–A' in the top views of FIGS. 3A and 3B. Further, a printed wiring board is formed from a two-layered structure in Embodiment Mode, and the respective layers are shown in FIGS. 3A and 3B.

In FIG. 3A, reference symbol 300 denotes a first printed wiring board, and a wiring 301 for aiding a current supply line (hereinafter referred to as current supply auxiliary line) is formed thereon. In the present specification, the current supply line is a wiring for supplying a current, which flows to an EL element, to each EL element, and the wiring for aiding the current supply line is a wiring that is connected in parallel to the current supply line in order to reduce the apparent wiring resistance of the current supply line. The wiring for aiding the current supply line can be made of a metallic film of copper, silver, gold, aluminum or nickel, or an alloy film containing as a main component a material selected from copper, silver, gold, aluminum, or nickel. Also, the wiring for aiding the current supply line can be formed into a layered structure made of a metallic film that is made of two or more different elements selected from copper, silver, gold, aluminum and nickel.

Further, a dotted line denoted by reference symbol 302 is a source driver circuit, dotted lines denoted by reference symbols 303a and 303b are gate driver circuits, and a dotted line denoted by reference symbol 304 is a pixel portion. These driver circuits and the pixel portion are formed on an element-formed substrate 330 (refer to FIG. 3C). In addition, a thick dotted line denoted by reference symbol 305 is a current supply line that is formed on the element-formed substrate 330. In a contact portion 306 at this point, the current supply auxiliary line 301 is electrically connected to a conductor 307, and further electrically connected to the current supply line 305 via the conductor 307.

Thus, the current supply auxiliary line 301 that is made of a low resistant material such as a copper foil is formed on the first printed wiring board 300. The current supply auxiliary line 301 is electrically connected to the current supply line 305, that is formed on the element-formed substrate 330, via the contact portion 306. Accordingly, it is possible to make the electric potential equal in any position of the current supply line 305, and therefore, the voltage drop of the current supply line 305 can be substantially suppressed.

In FIG. 3B, reference symbol 310 denotes a second printed wiring board, and a wiring 311 for aiding a gate control wiring (hereinafter referred to as gate control auxiliary line) is formed thereon. In the present specification, the gate control wiring is a wiring for transmitting a power source signal of the gate driver circuit, a clock signal, or a start signal, and the wiring for aiding the gate control wiring is a wiring that is connected in parallel to the gate control wiring in order to reduce the apparent wiring resistance of the gate control wiring.

Further, the thick dotted line denoted by reference symbol 312 is a gate control wiring that is formed on the element-formed substrate. At this point, the gate control auxiliary line 311 is electrically connected to a conductor 314 via a contact portion 313, and then further electrically connected to a gate control wiring 315 via the conductor 314.

Thus, the gate control auxiliary line 311 that is made of a low resistant material such as a copper foil is formed on the second printed wiring board 310. The gate control auxiliary line 311 is electrically connected to the gate control wiring 312 that is formed on the element-formed substrate 330 via the contact portion 313. Accordingly, it is possible to make the electric potential equal in any position of the gate control wiring 312, and therefore, the voltage drop of the gate control wiring 312 can be substantially suppressed.

In Embodiment Mode of the present invention, the first printed wiring board 300 and the second printed wiring board 310 are first adhered to each other (denoted as printed wiring board 320), and then the adhered boards are bonded with the element-formed substrate 330 by using a sealing agent 331. Either the first printed wiring board 300 or the second printed wiring board 310 is electrically connected to the element-formed substrate 330 through the conductor 307 or 314. It is to be noted that there is no limit to the position of providing the conductors 307 and 314.

In Embodiment Mode, the gap between the printed wiring board 320 and the element-formed substrate 330 is prescribed by the height of the anisotropic conductive film, conductive paste or bump. It is desirable that the gap is formed between 5 μm and 1 mm (preferably between 10 and 100 μm). If the gap is too narrow, then the printed wiring board 320 and the luminous element may be in contact with each other. On the other hand, if the gap is too wide, then it becomes difficult for the anisotropic conductive film, conductive paste, or bump to secure the gap. Note that a spacer or a filler used in a liquid crystal may be used to secure the gap.

Furthermore, an inert gas (preferably argon gas, neon gas, nitrogen gas, or helium gas) or resin may be filled in an airtight space 321 between the element-formed substrate 330 and the printed wiring board 320. As the resin, ultraviolet cured resin, thermosetting resin, silicone resin, epoxy resin, acrylic resin, polyimide resin, phenol resin, PVC (polyvinyl chloride), PVB (polyvinyl butylal), or EVA (ethylenevinyl acetate) may be used.

It is effective to provide a moisture absorbent material (typically barium oxide or cesium oxide) together with the inert gas or the resin in the interior of the airtight space 321.

An important point in Embodiment Mode of the present invention is that a low resistant wiring pattern provided in the printed wiring board is electrically connected to the current supply line 305 and the gate control wiring 312 which readily become the wiring resistant problem. Thus, the occurrence of the voltage drop caused by the wiring resistance of the current supply line 305 and the gate control wiring 312 can be suppressed, whereby an EL display device that may perform a homogeneous image display can be manufactured.

Embodiment 1

In Embodiment 1, an explanation will be made with reference to FIGS. 4A and 4B on an active matrix EL display device that is manufactured by employing the present invention. FIG. 4A is a top view of an element-formed substrate (denoted by reference symbol 400 in FIG. 4B) having an EL element formed thereon. Indicated by the dotted lines, reference symbol 401 denotes a source driver circuit, 402 denotes a gate driver circuit, and 403 denotes a pixel portion.

Further, reference symbol 404 denotes a printed wiring board, and a PWB side wiring 405 is formed thereon. The dotted line indicated by reference symbol 406 denotes a first sealing member, and in the inner side surrounded by the first sealing member 406, resin (denoted by reference symbol 407 in FIG. 4B) is provided between the printed wiring board 404 and the element-formed substrate 400.

It is to be noted that barium oxide (denoted by reference symbol 408 in FIG. 4B) is used as the moisture absorbent material doped into the resin 407.

Reference symbol 409 denotes a contact portion which electrically connects the PWB side wiring 405 and connecting wirings 410a to 410c that are formed on the element-formed substrate 400. An electric signal such as a video signal or a clock signal inputted from an FPC (Flexible Printed Circuit) 411, which serves as a connecting terminal with an external device, is transmitted to the PWB side wiring 405, and then is transmitted to the current supply line via the contact portion 409.

A cross-sectional view corresponding to the cross-section taken along the line A–A'of FIG. 4A is shown in FIG. 4B. It is to be noted that in FIGS. 4A and 4B, the same reference symbols are used to denote the same components. As shown in FIG. 4B, the pixel portion 403 and the source side driver circuit 401 are formed on the substrate 400. The pixel portion 403 is formed of a plurality of pixels each including a TFT 431 for controlling the current that flows to an EL element (hereinafter referred to as current control TFT) and a pixel electrode 432 electrically connected to the drain of the current control TFT 431. Further, the source side driver circuit 401 is formed using a CMOS circuit in which an N channel TFT 433 and a P channel TFT 434 are combined complementarily.

The pixel electrode 432 is formed of a transparent conducting film (a film made of a compound of indium oxide and tin oxide in Embodiment 1) and functions as an anode of the EL element. An insulating film 435 is formed on both ends of the pixel electrode 432 where a light-emitting layer 436a luminescing red, a light-emitting layer 436b luminescing green, and a light-emitting layer luminescing blue (not shown in the drawing) are further formed.

A light shielding conductive film (an alloy film of lithium and aluminum in Embodiment 1) is used to form a cathode 437 of the EL element that is further formed thereon.

Regarding the film deposition method of the light-emitting layers 436a and 436b, any known method may be used, and an organic material or an inorganic material can be used as the material for forming the light-emitting layers. The structure of the light-emitting layer do not have to only be the light-emitting layer, but may be a lamination structure in which an electron injection layer, an electron transportation layer, a hole transportation layer, and a hole injection layer are combined.

In case of Embodiment 1, the cathode 437 also functions as a common wiring shared by all the pixels, and is electrically connected to the connecting wirings 410a to 410c. The connecting wirings 410a to 410c are electrically connected to the PWB side wiring 405 by anisotropic conductive films 440a to 440c. Furthermore, because the PWB side wiring 405 is electrically connected to the FPC 411, as a result, the connecting wirings 410a to 410c become electrically connected to the FPC 411.

Note that in Embodiment 1, the first sealing member 406 is formed by using a dispenser or the like, and a spacer (not shown) is sprayed to bond the first sealing member 406 to the printed wiring board 404. The resin 407 is then filled into a space surrounded by the element-formed substrate 400, the printed wiring board 404, and the first sealing member 406. Although resin doped with barium oxide as the moisture absorbent material is used in Embodiment 1, the barium oxide can be sealed inside the resin in massive distributions. In addition, as the material of the not shown spacer, a moisture absorbent material may be used.

Next, after curing the resin 407 by ultraviolet irradiation or heat application, an opening portion (not shown) formed in the first sealing member 406 is closed. Then, a second sealing member 412 is disposed so as to cover a portion of the first sealing member 406, the printed wiring board 404, and the FPC 411. The second sealing member 412 may be formed of the same material as the first sealing member 406.

By sealing the EL element within the resin 407 using the method as described above, the EL element is completely cut off from external environment, and the invasion by substances such as moisture and oxygen from the outside which accelerate the oxidation degradation of the organic material thus can be prevented. Accordingly, an EL display device with high reliability can be manufactured.

Further, the occurrence of the voltage drop caused by the wiring resistance of the current supply line and the gate control wiring provided on the element-formed substrate can be suppressed by employing the present invention, whereby an EL display device that may perform a homogeneous image display can be manufactured.

Embodiment 2

Figure 5A:
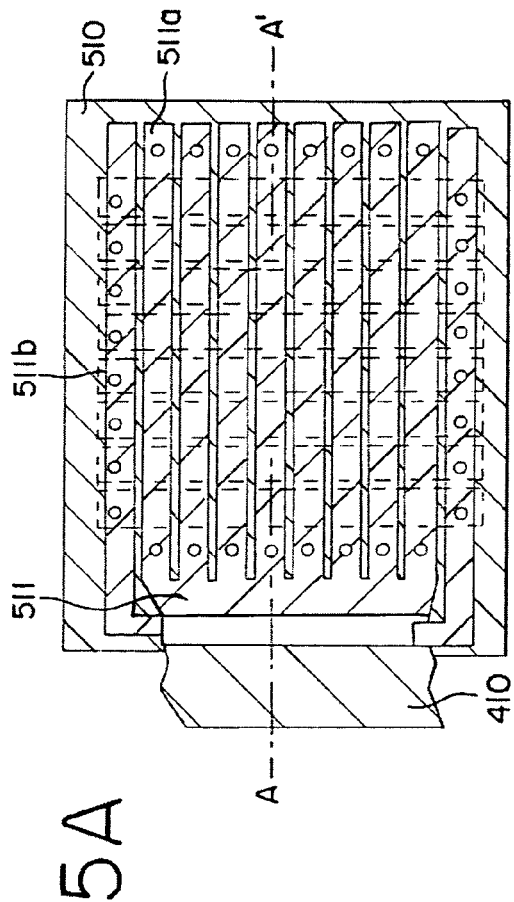
FIGS. 5A and 5B are diagrams showing a top structure and a cross-sectional structure of an EL display device, respectively.

In Embodiment 2, an explanation will be made with reference to FIGS. 5A and 5B on a passive matrix EL display device that is manufactured by employing the present invention. It is to be noted that FIG. 5A is a top view thereof and FIG. 5B is a cross-sectional view thereof taken along the line A–A'of FIG. 5A.

Figure 5B:
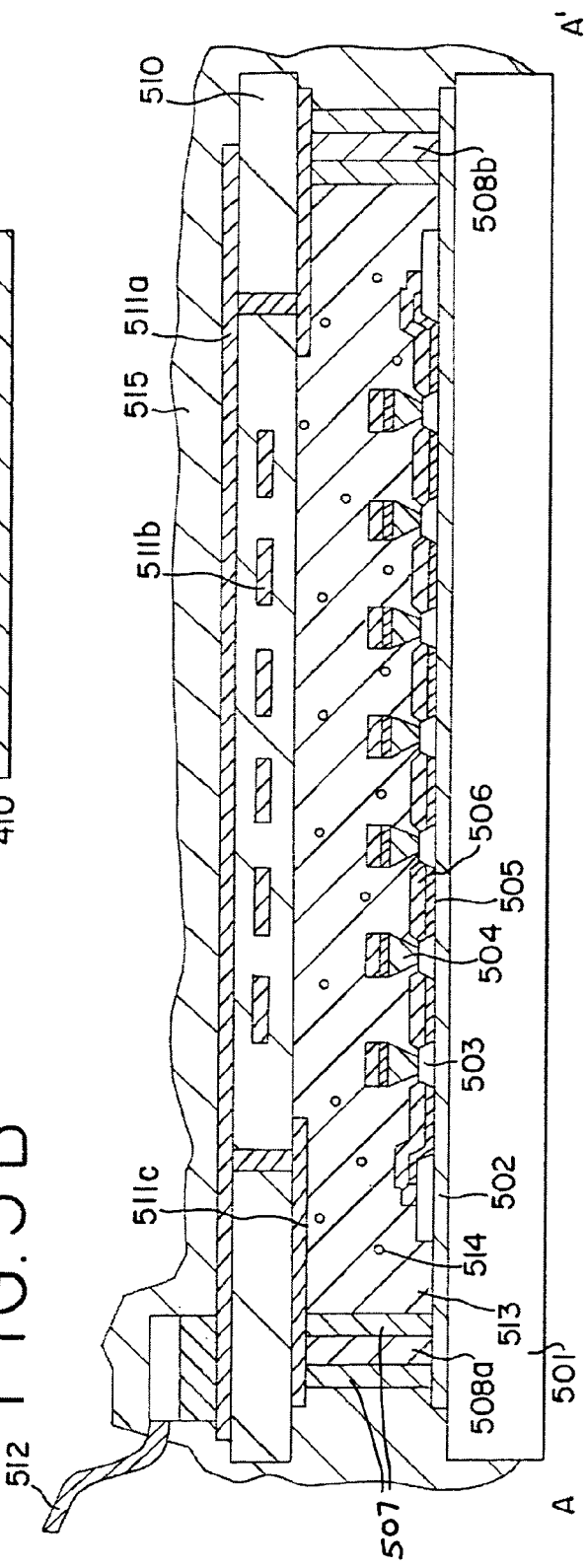

In FIG. 5B, reference symbol 501 denotes an element-formed substrate made of plastic, and reference symbol 502 denotes an a node made of a compound of indium oxide and zinc oxide. In Embodiment 2, the anode 502 is formed by the evaporation method. Though not shown in FIGS. 5A and 5B, it is to be noted that a plurality of anodes are arranged in stripe shapes in a parallel direction in a defined space.

An insulating film 503 is formed such that it is orthogonal to the plurality of anodes 502 arranged in stripe shapes. In addition, the insulating film 503 is also provided in the gaps of the anodes 502 in order to insulate each of the anodes 502 separately. Therefore, the insulating film 503 is patterned into matrix when observed from the top.

Further, a bank 504 made of resin is formed on the insulating film 503. The bank 504 is formed in a perpendicular direction in the space such that it is orthogonal to the anodes 502. The shape of the bank 504 is processed into an inverted triangle (inverted taper shape). Note that the structure may be a two-layered structure where the upper layer having an eaves-shape is on the lower layer.

Thereafter, a light-emitting layer 505 and a cathode 506 made of an aluminum alloy are formed in succession. It is preferable to successively form both the light-emitting layer 505 and the cathode 506 under a vacuum or inert atmosphere because the light-emitting layer 505 is easily affected by moisture and oxygen.

The light-emitting layer 505 may be formed of any known material.

However, a polymer-based organic material is preferred from the viewpoint of an easy and simple film deposition. Also, it is preferable that the cathode 506 is formed by the evaporation method.

The light-emitting layer 505 and the cathode 506 are both formed in the grooves which are formed by the bank 504. Both are arranged in stripe shapes in a perpendicular direction in the defined space.

Though not shown in the figures, it is effective to provide a hole transportation layer or a hole injection layer as a buffer layer between the light-emitting layer 505 and the cathode 506. Material such as copper pthalocyanine, polythiophene, or PEDOT can be used as the hole injection layer.

Thus, an EL element is formed on the element-formed substrate 501 by the above described method. Note that because the bottom electrode serves as a transmissive anode in Embodiment 2, the light generated in the light-emitting layer 505 is irradiated in a direction towards the bottom surface (in the direction towards the element-formed substrate 501) in the defined space.

The anodes 502 are electrically connected to a PWB side wiring 511 that is formed on a printed wiring board 510 by anisotropic conductive films 508a and 508b which are provided inside a first sealing member 507. In Embodiment 2, the PWB side wiring 511 is a three-layered structure made up of a wiring 511a provided on the front surface of the printed wiring board 510, a wiring 511b provided in the interior thereof, and a wiring 511c provided on the back surface thereof. The materials cited in the explanation of FIG. 1 can be used as the material to form the printed wiring board 510.

At this point, as shown in FIG. 5A, the wiring 511a provided on the front surface of the printed wiring board 510 and the wiring 511b provided in the interior thereof are formed such that they are orthogonal to each other. The wiring 511a provided on the front surface of the printed wiring board 510 is electrically connected to the anodes 502, and the wiring 511c provided on the back surface thereof is electrically connected to the cathode 506.

Further, the wiring 511a provided on the front surface of the printed wiring board 510 is electrically connected to an FPC 512 to thereby transmit a signal from an external equipment.

In Embodiment 2, the space between the element-formed substrate 501 and the printed wiring board 510 is provided with a resin 513 and a moisture absorbent material 514 that is doped into the resin 513 to thereby protect the EL element from moisture and oxygen. Of course, the space may be filled with inert gas instead of filling the space with the resin. In addition, a second sealing member 515 is provided so as to cover the entire printed wiring board 510 to thereby suppress the deterioration of the EL element.

By sealing the EL element within the resin 513 using the method as described above, the EL element is completely cut off from external environment, and the invasion by substances such as moisture and oxygen from the outside which accelerate the oxidation degradation of the organic material thus can be prevented. Accordingly, an EL display device with high reliability can be manufactured.

Further, the occurrence of the voltage drop caused by the wiring resistance of the anodes and cathodes provided on the element-formed substrate can be suppressed by employing the present invention, whereby an EL display device that may perform a homogeneous image display can be manufactured.

Embodiment 3

Figure 6:
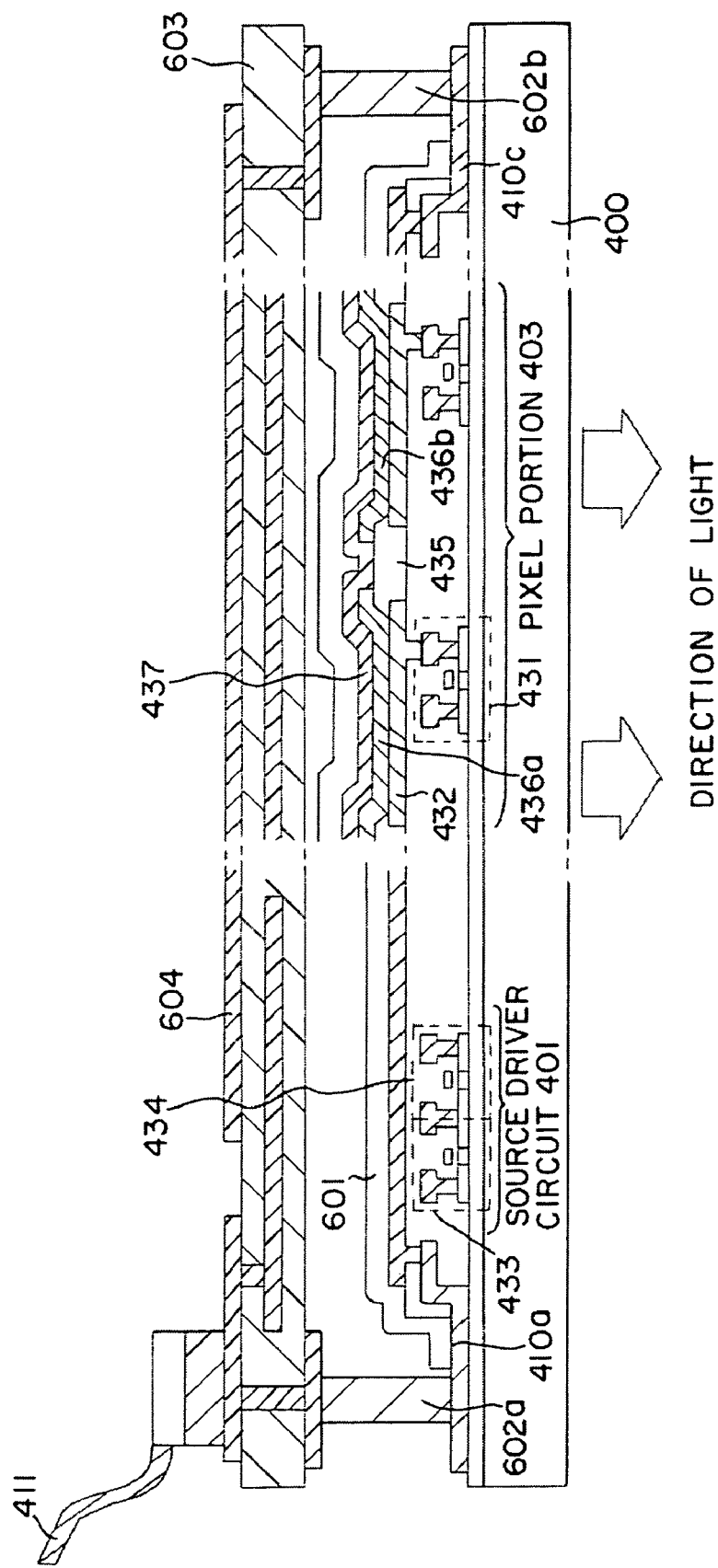
FIG. 6 is a diagram showing a cross-sectional structure of an EL display device.

Shown in Embodiment 3 is a modified example of the structure of the EL display device described in Embodiment 1. The description thereof will be made with reference to FIG. 6. Structures of a TFT and an EL element formed on the element-formed substrate 400 are the same as those of FIGS. 4A and 4B. Therefore, only different components will be denoted with reference symbols and explained.

Upon forming a structure similar to that of Embodiment 1 up to the formation of the cathode 437, a passivation film 601 is further formed to a thickness of 50 to 500 nm (preferably between 300 and 400 nm) to cover the cathode 437. As the passivation film 601, a tantalum oxide film, a silicon nitride film, a silicon oxide film, a silicon oxide nitride film, or a lamination film of a combination thereof may be used. It is preferable that the film deposition thereof is performed at a temperature of 150° C. or less by vapor-phase deposition such that the EL element will not deteriorate.

The sealing of the EL element is completed by the passivation film 601 in Embodiment 3. That is, the EL element is protected from external substances such as moisture and oxygen by the passivation film 601, and hence Embodiment 3 is characterized in that the reliability of the EL display device is enhanced. Accordingly, though the structure shown in FIGS. 4A and 4B is one in which the EL element is sealed by the resin 407 for protection from external substances, in Embodiment 3, there is no need to particularly perform such sealing. As a result, the structure of the EL display device can be simplified.

At this point, anisotropic conductive films 602a and 602b are not only electrically connected to the connecting wirings 410a to 410c and a PWB side wiring 604 that is formed on a printed wiring board 603, but also carry the role of a spacer for determining the gap between the element-formed substrate 400 and the printed wiring board 603. Of course, a separate spacer may be provided.

By sealing the EL element with the passivation film 601 using the method as described above, the EL element is completely cut off from external environment, and the invasion by substances such as moisture and oxygen from the outside which accelerate the oxidation degradation of the organic material thus can be prevented. Accordingly, an EL display device with high reliability can be manufactured.

Further, the occurrence of the voltage drop caused by the wiring resistance of the current supply line and the gate control wiring provided on the element-formed substrate can be suppressed by employing the present invention, whereby an EL display device that may perform a homogeneous image display can be manufactured.

Note that the constitution of Embodiment 3 may be combined with the constitution of Embodiment 1.

Embodiment 4

Figure 7:
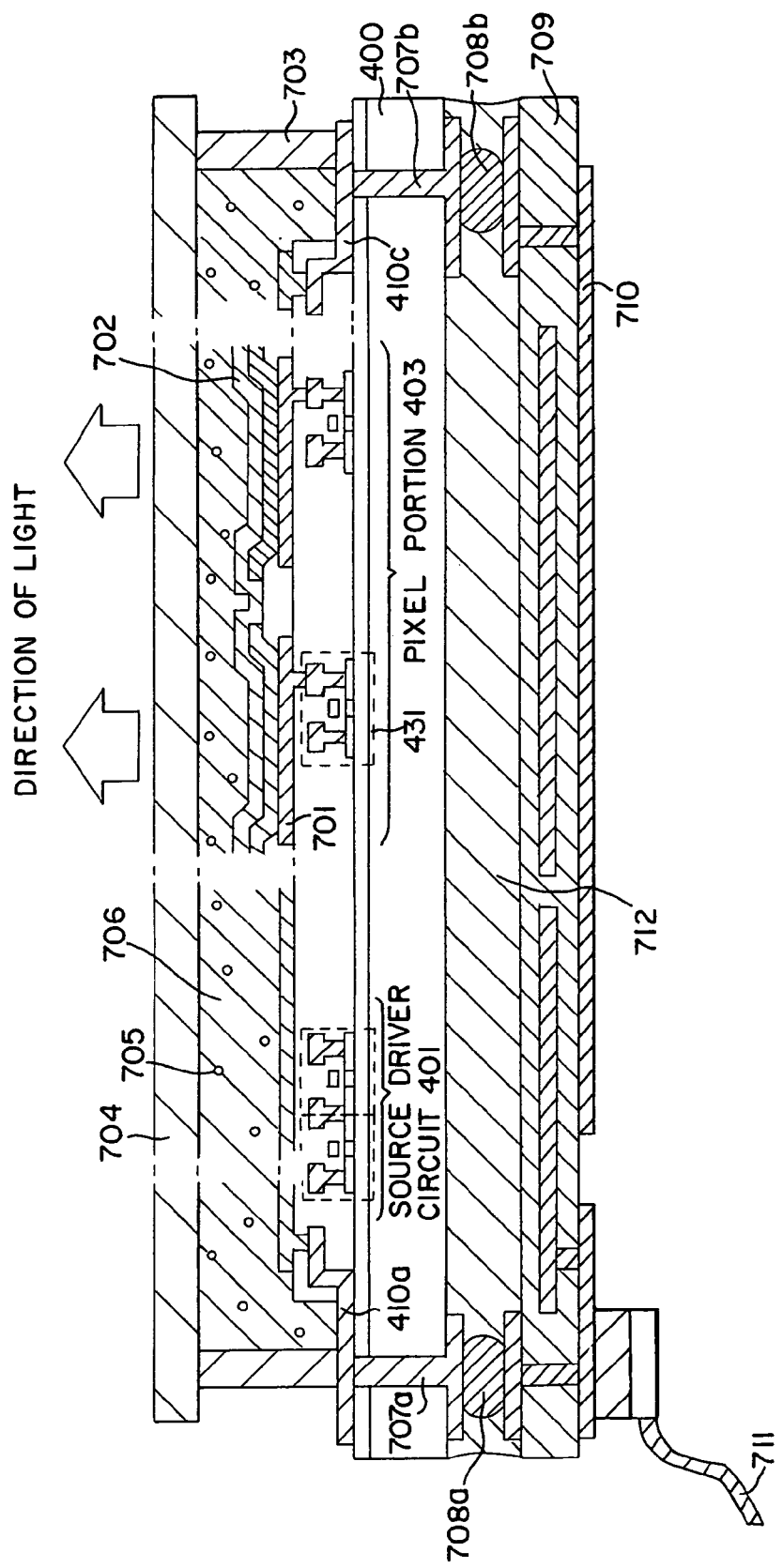
FIG. 7 is a diagram showing a cross-sectional structure of an EL display device.

Shown in Embodiment 4 is a modified example of the structure of the EL display device described in Embodiment 1. The description thereof will be made with reference to FIG. 7. Structures of a TFT and an EL element formed on the element-formed substrate 400 are basically the same as those of FIGS. 4A and 4B. Therefore, only different components will be denoted with reference symbols and explained.

In Embodiment 4, the structure of the EL element is a reversed one from that of FIGS. 4A and 4B. A light shielding conductive film (an aluminum alloy film in Embodiment 4) is used as a pixel electrode (cathode) 701, and a transparent conductive film (a compound film of indium oxide and zinc oxide in Embodiment 4) is used as an anode 702. Thus, the direction of the light emitted is a direction towards the upper part of the diagram (direction indicated by an arrow).

Upon completion of the EL element, a covering member 704 is bonded by a first sealing member 703, and the inside thereof is provided with a resin 706 that is doped with a moisture absorbent material 705. A transmissive material can be used as the covering member 704, and a resin film, a resin substrate, a plastic substrate, a glass substrate, or a quartz substrate may be used.

Next, a via hole is formed from the back surface of the element-formed substrate 400 to thereby form connecting wirings 707a and 707b. The connecting wirings 707a and 707b are further electrically connected to a PWB side wiring 710 that is formed on a printed wiring board 709 via bumps 708a and 708b which are made of gold, solder, or nickel. The PWB side wiring 710 is electrically connected to an FPC 711. It is to be noted that reference symbol 712 denotes a resin for bonding the element-formed substrate 400 and the printed wiring board 709. However, it may be a structure without the provision of the resin 712.

The occurrence of the voltage drop caused by the wiring resistance of the current supply line and the gate control wiring provided on the element-formed substrate can be suppressed by employing the structure of Embodiment 4, whereby an EL display device that may perform a homogeneous image display can be manufactured.

Embodiment 5

Examples of the light-emitting device employing the EL element were explained in Embodiments 1 through 4. However, the present invention may also be employed in an EC (Electro Chromic) display device, a field emission display (FED) or a light-emitting device having a light-emitting diode that employs a semiconductor.

Embodiment 6

The light-emitting device formed by implementing the present invention has superior visibility in bright locations in comparison to a liquid crystal display device because it is a self-emissive type device, and moreover its angle of vision is wide. Accordingly, it can be used as a display portion for various electronic equipment.

For example, for appreciation of TV broadcasts by large screen, it is appropriate to use a display of the present invention incorporating the light-emitting device in its casing and having a diagonal equal to 20 to 60 inches.

Note that all displays for exhibiting information such as a personal computer display, a TV broadcast reception display, or an advertisement display are included as the display incorporating a light-emitting device in its casing. Further, the light emitting device of the present invention can be used as a display portion of the other various electronic equipment.

The following can be given as examples of such electronic equipment: a video camera; a digital camera; a goggle type display (head mounted display); a car navigation system; an audio reproducing device (such as a car audio system, an audio component system); a notebook personal computer; a game equipment; a portable information terminal (such as a mobile computer, a mobile telephone, a mobile game equipment or an electronic book); and an image playback device provided with a recording medium (specifically, a device which performs playback of a recording medium and is provided with a display which can display those images, such as a digital video disk (DVD)). In particular, because portable information terminals are often viewed from a diagonal direction, the wideness of the angle of vision is regarded as very important. Thus, it is preferable that the EL display device is employed. Examples of these electronic equipment are shown in FIGS. 8 and 9.

Figure 8A:
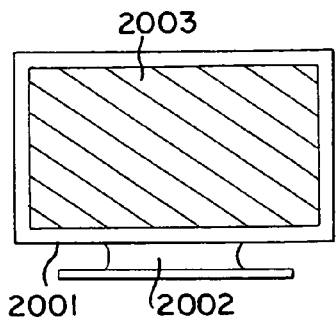
FIGS. 8A to 8F are views showing electric equipments of the present invention.

FIG. 8A is a display incorporating a light-emitting device in its casing, containing a casing 2001, a support stand 2002, and a display portion 2003. The present invention can be used in the display portion 2003. Since the display is a self-emissive type device without the need of a backlight, its display portion can be made thinner than a liquid crystal display device.

Figure 8B:
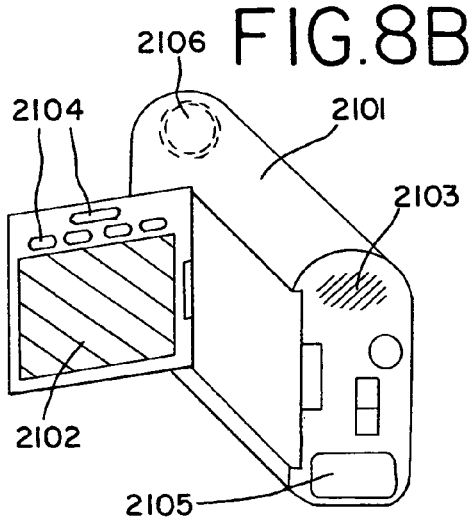

FIG. 8B is a video camera, containing a main body 2101, a display portion 2102, a voice input portion 2103, operation switches 2104, a battery 2105, and an image receiving portion 2106. The light emitting device of the present invention can be used in the display portion 2102.

Figure 8C:
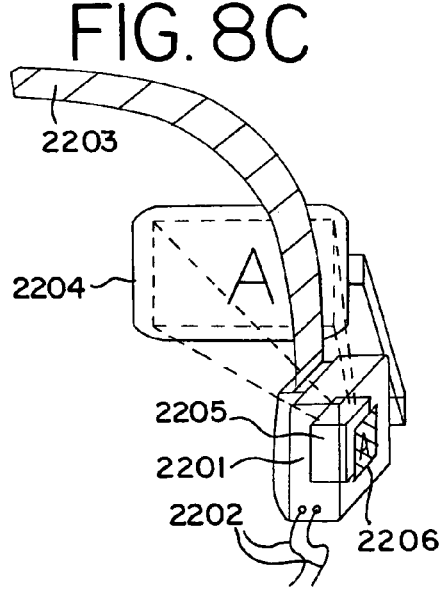

FIG. 8C is a portion of a head fitting type EL display (right side), containing a main body 2201, a signal cable 2202, a head fixing band 2203, a display portion 2204, an optical system 2205, and a light emitting device 2206. The present invention can be used in the light emitting device 2206.

Figure 8D:
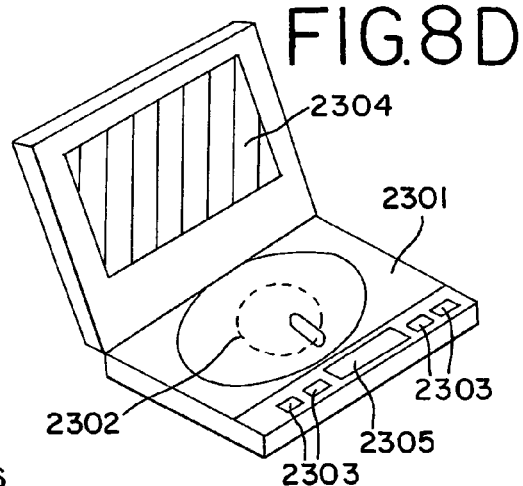

FIG. 8D is an image playback device (specifically, a DVD playback device) provided with a recording medium, containing a main body 2301, a recording medium (such as a DVD) 2302, operation switches 2303, a display portion (a) 2304, and a display portion (b) 2305. The display portion (a) is mainly used for displaying image information, and the image portion (b) is mainly used for displaying character information, and the light emitting device of the present invention can be used in these image portions (a) and (b). Note that domestic game equipment is included as the image playback device provided with a recording medium.

Figure 8E:
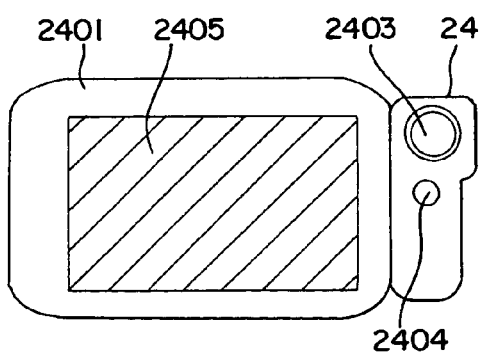

FIG. 8E is a mobile computer, containing a main body 2401, a camera portion 2402, an image receiving portion 2403, operation switches 2404, and a display portion 2405. The light emitting device of the present invention can be used in the display portion 2405.

Figure 8F:
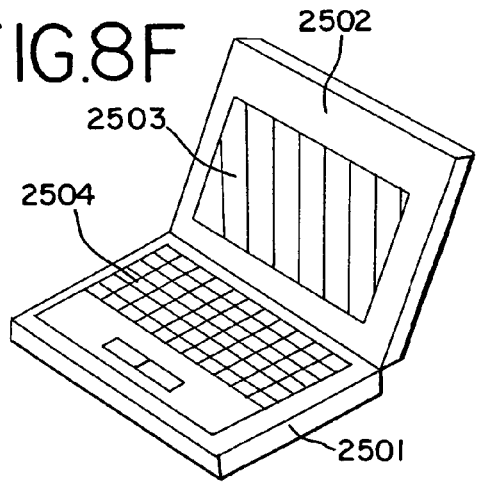

FIG. 8F is a personal computer, containing a main body 2501, a casing 2502, a display portion 2503, and a keyboard 2504. The light emitting device of the present invention can be used in the display portion 2503.

Note that in the future if the emission luminance becomes higher, the projection of light including outputted images can be enlarged by lenses, optical fiber, or the like. Then it will become possible to use the light emitting device in a front type or a rear type projector.

The emitting portion of the light emitting device consumes power, and therefore it is preferable to display information so as to have the emitting portion become as small as possible. Therefore, when using the light emitting device in a display portion which mainly displays character information, such as a portable information terminal, in particular, a portable telephone and an audio reproducing device, it is preferable to drive it by setting non-emitting portions as background and forming character information in emitting portions.

Figure 9A:
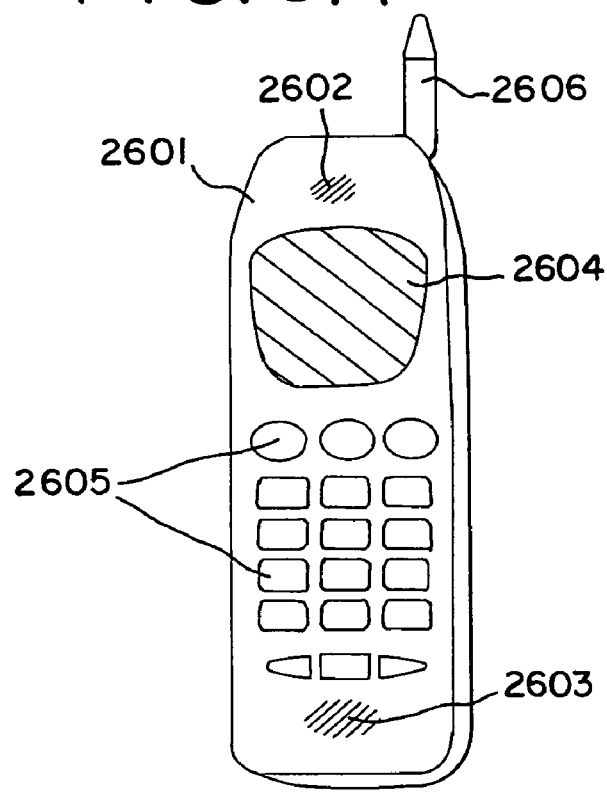
FIGS. 9A and 9B are views showing electric equipments of the present invention.

FIG. 9A is a portable telephone, containing a main body 2601, a voice output portion 2602, a voice input portion 2603, a display portion 2604, operation switches 2605, and an antenna 2606. The light emitting device of the present invention can be used in the display portion 2604. Note that by displaying white characters in a black background in the display portion 2604, the power consumption of the portable telephone can be reduced.

Figure 9B:
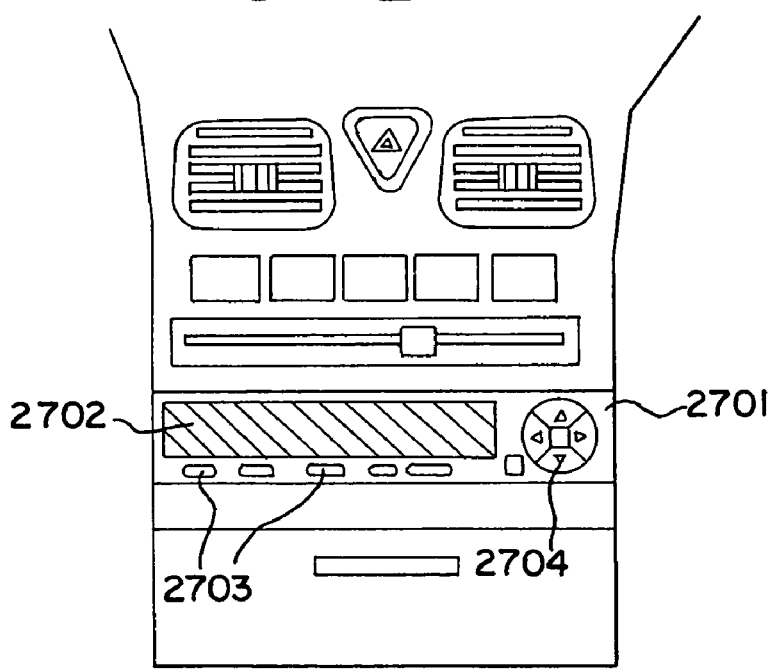

FIG. 9B is an audio reproducing device, specifically a car audio system, containing a main body 2701, a display portion 2702, and operation switches 2703 and 2704. The light emitting device of the present invention can be used in the display portion 2702. Furthermore, an audio reproducing device for a car is shown in Embodiment 6, but it may also be used for a mobile type and a domestic type of audio reproducing device. Note that by displaying white characters in a black background in the display portion 2704, the power consumption can be reduced. This is particularly effective in a mobile type audio reproducing device.

The range of applications of the present invention is thus extremely wide, and it is possible to apply the present invention to electronic equipment in all fields. Furthermore, any constitution of the light emitting device shown in Embodiments 1 to 6 may be employed in the electronic equipment of this embodiment.

Embodiment 7

In the case that an electric equipment having a light-emitting device according to the present invention as a display portion is used outdoors, of course the display portion is viewed sometimes when it is dark and sometimes when it is light. Though, when it is dark, what is displayed can be sufficiently recognized even if the luminance is not so high, when it is light, what is displayed may not be recognized if the luminance is not high.

With regard to a light-emitting device, since the luminance varies in proportion to the current or the voltage for operating the element, if the luminance is required to be higher, the power consumption has to be increased accordingly. However, if the level of the luminance of light emission is adjusted to be so high, when it is dark, the display is much brighter than needed with the power consumption being unnecessarily large.

In order to provide for such a case, it is effective to provide a light-emitting device according to the present invention with a function to sense with a sensor the brightness of the environment and to adjust the luminance of light emission according to the degree of the brightness. More specifically, the luminance of light emission is made high when it is light, while the luminance of light emission is made low when it is dark. As a result, a light-emitting device which can prevent the power consumption from increasing and which does not make the user feel fatigued can be realized.

It is to be noted that, as such a sensor for sensing the brightness of the environment, a CMOS sensor or a CCD (charge-coupled device) can be used. Such a CMOS sensor may be conventionally integrated on a substrate where a light emitting element is formed, or a semiconductor chip may be attached to the outside. Further, a semiconductor chip having such a CCD formed thereon may be attached to a substrate where a light emitting element is formed, or a part of the electric equipment having the light-emitting device as its display portion may be structured to be provided with the CCD or the CMOS sensor.

A control circuit for changing the current or the voltage for operating the light emitting element in response to a signal obtained by the sensor for sensing the brightness of the environment is provided, by which the luminance of light emission of the light-emitting element can be adjusted according to the brightness of the environment.

It is to be noted that such adjustment may be made either automatically or manually.

It is to be noted that the structure of the present embodiment can be implemented in any electric equipment described in Embodiment 6.

In the active matrix type or the passive type of light-emitting device, the delay of a signal and the voltage drop due to a wiring resistance are reduced to thereby enhance the operating speed of the driver circuit portion and improve the homogeneity of the quality of the image in the pixel portion.

What is claimed is:

1. A display device comprising:
   a first substrate;
   a light emitting element over the first substrate comprising:
      a first electrode;
      a second electrode adjacent to the first electrode; and
      a light emitting material interposed between the first electrode and the second electrode;
   a current supply line over the first substrate, electrically connected to the first electrode;
   a second substrate; and
   an auxiliary wiring adjacent to the second substrate,
   wherein the auxiliary wiring is electrically connected to the first electrode via the current supply line in a first connecting portion, and
   wherein the auxiliary wiring is electrically connected to the first electrode via the current supply line in a second connecting portion.

2. A display device according to claim 1, wherein the auxiliary wiring comprises a metal selected from the group consisting of a copper, a silver, a gold, an aluminum and a nickel.

3. A display device according to claim 1, wherein a part of the auxiliary wiring is located in the second substrate.

4. A display device according to claim 1, wherein the auxiliary wiring is electrically connected to the current supply line via a conductive material.

5. A display device comprising:
   a first substrate;
   a light emitting element over the first substrate:
      a first electrode;
      a second electrode adjacent to the first electrode; and
      a light emitting material interposed between the first electrode and the second electrode;
   a current supply line over the first substrate, electrically connected to the first electrode;
   an insulating layer over the light emitting element;
   a second substrate; and
   an auxiliary wiring adjacent to the second substrate,
   wherein the auxiliary wiring is electrically connected to the first electrode via the current supply line, and
   wherein the insulating layer is located between the current supply line and the auxiliary wiring.

6. A display device according to claim 5, wherein the auxiliary wiring comprises a metal selected from the group consisting of a copper, a silver, a gold, an aluminum and a nickel.

7. A display device according to claim 5, wherein a part of the auxiliary wiring is located in the second substrate.

8. A display device according to claim 5, wherein the auxiliary wiring is electrically connected to the current supply line via a conductive material.

9. A display device according to claim 5, wherein the insulating layer is a resin material.

10. A display device according to claim 9, wherein the resin material comprises a moisture absorbent material.

11. A display device according to claim 5, wherein the insulating layer is a passivation film.

12. A display device comprising:
   a first substrate;
   a light emitting element over the first substrate:
      a first electrode;
      a second electrode adjacent to the first electrode; and
      a light emitting material interposed between the first electrode and the second electrode;
   a current supply line over the first substrate, electrically connected to the first electrode;
   an insulating layer over the light emitting element;
   a second substrate; and
   an auxiliary wiring adjacent to the second substrate,
   wherein the auxiliary wiring is electrically connected to the first electrode via the current supply line, and wherein the first substrate is located between the current supply line and the auxiliary wiring.

13. A display device according to claim 12, wherein the auxiliary wiring comprises a metal selected from the group consisting of a copper, a silver, a gold, an aluminum and a nickel.

14. A display device according to claim 12, wherein a part of the auxiliary wiring is located in the second substrate.

15. A display device according to claim 12, wherein the auxiliary wiring is electrically connected to the current supply line via a conductive material.

16. A display device according to claim 12, wherein the insulating layer is a resin material.

17. A display device according to claim 16, wherein the resin material comprises a moisture absorbent material.

18. A display device according to claim 12, wherein the insulating layer is a passivation film.

19. A camera comprising a display device comprising:
a first substrate;
a light emitting element over the first substrate:
  a first electrode;
  a second electrode adjacent to the first electrode; and
  a light emitting material interposed between the first electrode and the second electrode;
a current supply line over the first substrate, electrically connected to the first electrode;
a second substrate; and
an auxiliary wiring adjacent to the second substrate,
wherein the auxiliary wiring is electrically connected to the first electrode via the current supply line in a first connecting portion, and
wherein the auxiliary wiring is electrically connected to the first electrode via the current supply line in a second connecting portion.

20. A camera comprising a display device according to claim 19, wherein the auxiliary wiring comprises a metal selected from the group consisting of a copper, a silver, a gold, an aluminum and a nickel.

21. A camera comprising a display device according to claim 19, wherein a part of the auxiliary wiring is located in the second substrate.

22. A camera comprising a display device according to claim 19, wherein the auxiliary wiring is electrically connected to the current supply line via a conductive material.

23. A camera comprising a display device comprising:
a first substrate;
a light emitting element over the first substrate:
  a first electrode;
  a second electrode adjacent to the first electrode; and
  a light emitting material interposed between the first electrode and the second electrode;
a current supply line over the first substrate, electrically connected to the first electrode;
an insulating layer over the light emitting element;
a second substrate; and
an auxiliary wiring adjacent to the second substrate,
wherein the auxiliary wiring is electrically connected to the first electrode via the current supply line, and
wherein the insulating layer is located between the current supply line and the auxiliary wiring.

24. A camera comprising a display device according to claim 23, wherein the auxiliary wiring comprises a metal selected from the group consisting of a copper, a silver, a gold, an aluminum and a nickel.

25. A camera comprising a display device according to claim 23, wherein a part of the auxiliary wiring is located in the second substrate.

26. A camera comprising a display device according to claim 23, wherein the auxiliary wiring is electrically connected to the current supply line via a conductive material.

27. A camera comprising a display device according to claim 23, wherein the insulating layer is a resin material.

28. A camera comprising a display device according to claim 27, wherein the resin material comprises a moisture absorbent material.

29. A camera comprising a display device according to claim 23, wherein the insulating layer is a passivation film.

30. A camera comprising a display device comprising:
a first substrate;
a light emitting element over the first substrate:
  a first electrode;
  a second electrode adjacent to the first electrode; and
  a light emitting material interposed between the first electrode and the second electrode;
a current supply line over the first substrate, electrically connected to the first electrode;
an insulating layer over the light emitting element;
a second substrate; and
an auxiliary wiring adjacent to the second substrate,
wherein the auxiliary wiring is electrically connected to the first electrode via the current supply line, and
wherein the first substrate is located between the current supply line and the auxiliary wiring.

31. A camera comprising a display device according to claim 30, wherein the auxiliary wiring comprises a metal selected from the group consisting of a copper, a silver, a gold, an aluminum and a nickel.

32. A camera comprising a display device according to claim 30, wherein a part of the auxiliary wiring is located in the second substrate.

33. A camera comprising a display device according to claim 30, wherein the auxiliary wiring is electrically connected to the current supply line via a conductive material.

34. A camera comprising a display device according to claim 30, wherein the insulating layer is a resin material.

35. A camera comprising a display device according to claim 34, wherein the resin material comprises a moisture absorbent material.

36. A camera comprising a display device according to claim 30, wherein the insulating layer is a passivation film.

37. A personal computer comprising a display device comprising:
a first substrate;
a light emitting element over the first substrate:
  a first electrode;
  a second electrode adjacent to the first electrode; and
  a light emitting material interposed between the first electrode and the second electrode;
a current supply line over the first substrate, electrically connected to the first electrode;
a second substrate; and
an auxiliary wiring adjacent to the second substrate,
wherein the auxiliary wiring is electrically connected to the first electrode via the current supply line in a first connecting portion, and
wherein the auxiliary wiring is electrically connected to the first electrode via the current supply line in a second connecting portion.

38. A personal computer comprising a display device according to claim 19, wherein the auxiliary wiring comprises a metal selected from the group consisting of a copper, a silver, a gold, an aluminum and a nickel.

39. A personal computer comprising a display device according to claim 19, wherein a part of the auxiliary wiring is located in the second substrate.

40. A personal computer comprising a display device according to claim 19, wherein the auxiliary wiring is electrically connected to the current supply line via a conductive material.

41. A personal computer comprising a display device comprising:
    a first substrate;
    a light emitting element over the first substrate:
       a first electrode;
       a second electrode adjacent to the first electrode; and
       a light emitting material interposed between the first electrode and the second electrode;
    a current supply line over the first substrate, electrically connected to the first electrode;
    an insulating layer over the light emitting element;
    a second substrate; and
    an auxiliary wiring adjacent to the second substrate,
    wherein the auxiliary wiring is electrically connected to the first electrode via the current supply line, and
    wherein the insulating layer is located between the current supply line and the auxiliary wiring.

42. A personal computer comprising a display device according to claim 41, wherein the auxiliary wiring comprises a metal selected from the group consisting of a copper, a silver, a gold, an aluminum and a nickel.

43. A personal computer comprising a display device according to claim 41, wherein a part of the auxiliary wiring is located in the second substrate.

44. A personal computer comprising a display device according to claim 41, wherein the auxiliary wiring is electrically connected to the current supply line via a conductive material.

45. A personal computer comprising a display device according to claim 41, wherein the insulating layer is a resin material.

46. A personal computer comprising a display device according to claim 45, wherein the resin material comprises a moisture absorbent material.

47. A personal computer comprising a display device according to claim 41, wherein the insulating layer is a passivation film.

48. A personal computer comprising a display device comprising:
    a first substrate;
    a light emitting element over the first substrate:
       a first electrode;
       a second electrode adjacent to the first electrode; and
       a light emitting material interposed between the first electrode and the second electrode;
    a current supply line over the first substrate, electrically connected to the first electrode;
    an insulating layer over the light emitting element;
    a second substrate; and
    an auxiliary wiring adjacent to the second substrate,
    wherein the auxiliary wiring is electrically connected to the first electrode via the current supply line, and
    wherein the first substrate is located between the current supply line and the auxiliary wiring.

49. A personal computer comprising a display device according to claim 48, wherein the auxiliary wiring comprises a metal selected from the group consisting of a copper, a silver, a gold, an aluminum and a nickel.

50. A personal computer comprising a display device according to claim 48, wherein a part of the auxiliary wiring is located in the second substrate.

51. A personal computer comprising a display device according to claim 48, wherein the auxiliary wiring is electrically connected to the current supply line via a conductive material.

52. A personal computer comprising a display device according to claim 48, wherein the insulating layer is a resin material.

53. A personal computer comprising a display device according to claim 52, wherein the resin material comprises a moisture absorbent material.

54. A personal computer comprising a display device according to claim 48, wherein the insulating layer is a passivation film.

55. A portable telephone comprising a display device comprising:
    a first substrate;
    a light emitting element over the first substrate:
       a first electrode;
       a second electrode adjacent to the first electrode; and
       a light emitting material interposed between the first electrode and the second electrode;
    a current supply line over the first substrate, electrically connected to the first electrode;
    a second substrate; and
    an auxiliary wiring adjacent to the second substrate,
    wherein the auxiliary wiring is electrically connected to the first electrode via the current supply line in a first connecting portion, and
    wherein the auxiliary wiring is electrically connected to the first electrode via the current supply line in a second connecting portion.

56. A portable telephone comprising a display device according to claim 55, wherein the auxiliary wiring comprises a metal selected from the group consisting of a copper, a silver, a gold, an aluminum and a nickel.

57. A portable telephone comprising a display device according to claim 55, wherein a part of the auxiliary wiring is located in the second substrate.

58. A portable telephone comprising a display device according to claim 55, wherein the auxiliary wiring is electrically connected to the current supply line via a conductive material.

59. A portable telephone comprising a display device comprising:
    a first substrate;
    a light emitting element over the first substrate:
       a first electrode;
       a second electrode adjacent to the first electrode; and
       a light emitting material interposed between the first electrode and the second electrode;
    a current supply line over the first substrate, electrically connected to the first electrode;
    an insulating layer over the light emitting element;
    a second substrate; and
    an auxiliary wiring adjacent to the second substrate,
    wherein the auxiliary wiring is electrically connected to the first electrode via the current supply line, and
    wherein the insulating layer is located between the current supply line and the auxiliary wiring.

60. A portable telephone comprising a display device according to claim 59, wherein the auxiliary wiring comprises a metal selected from the group consisting of a copper, a silver, a gold, an aluminum and a nickel.

61. A portable telephone comprising a display device according to claim 59, wherein a part of the auxiliary wiring is located in the second substrate.

62. A portable telephone comprising a display device according to claim 59, wherein the insulating layer is a resin material.

63. A portable telephone comprising a display device according to claim 62, wherein the resin material comprises a moisture absorbent material.

64. A portable telephone comprising a display device according to claim 59, wherein the auxiliary wiring is electrically connected to the current supply line via a conductive material.

65. A portable telephone comprising a display device according to claim 59, wherein the insulating layer is a passivation film.

66. A portable telephone comprising a display device comprising:
   a first substrate;
   a light emitting element over the first substrate:
      a first electrode;
      a second electrode adjacent to the first electrode; and
      a light emitting material interposed between the first electrode and the second electrode;
   a current supply line over the first substrate, electrically connected to the first electrode;
   an insulating layer over the light emitting element;
   a second substrate; and
   an auxiliary wiring adjacent to the second substrate,
   wherein the auxiliary wiring is electrically connected to the first electrode via the current supply line, and
   wherein the first substrate is located between the current supply line and the auxiliary wiring.

67. A portable telephone comprising a display device according to claim 66, wherein the auxiliary wiring comprises a metal selected from the group consisting of a copper, a silver, a gold, an aluminum and a nickel.

68. A portable telephone comprising a display device according to claim 66, wherein a part of the auxiliary wiring is located in the second substrate.

69. A portable telephone comprising a display device according to claim 66, wherein the auxiliary wiring is electrically connected to the current supply line via a conductive material.

70. A portable telephone comprising a display device according to claim 66, wherein the insulating layer is a resin material.

71. A portable telephone comprising a display device according to claim 70, wherein the resin material comprises a moisture absorbent material.

72. A portable telephone comprising a display device according to claim 66, wherein the insulating layer is a passivation film.

* * * * *

UNITED STATES PATENT AND TRADEMARK OFFICE
CERTIFICATE OF CORRECTION

PATENT NO. : 7,145,289 B2  Page 1 of 1
APPLICATION NO. : 11/083189
DATED : December 5, 2006
INVENTOR(S) : Shunpei Yamazaki and Takeshi Fukunaga It is certified that error appears in the above-identified patent and that said Letters Patent is hereby corrected as shown below:

Title Page, Inventors:
Please delete "(76)" insert --(75)-- before Inventors.

Title Page
Please insert --(73) Assignee: Semiconductor Energy Laboratory Co., Ltd., Kanagawa-ken (JP)--.

Signed and Sealed this

Seventeenth Day of February, 2009

JOHN DOLL
*Acting Director of the United States Patent and Trademark Office*